United States Patent [19]

Lombardo et al.

[11] 4,318,483

[45] Mar. 9, 1982

[54] AUTOMATIC RELATIVE DROPLET CHARGING TIME DELAY SYSTEM FOR AN ELECTROSTATIC PARTICLE SORTING SYSTEM USING A RELATIVELY MOVEABLE STREAM SURFACE SENSING SYSTEM

[75] Inventors: Igino Lombardo, Sharon; Donald E. Barry, Norwood, both of Mass.

[73] Assignee: Ortho Diagnostics, Inc., Raritan, N.J.

[21] Appl. No.: 68,259

[22] Filed: Aug. 20, 1979

[51] Int. Cl.³ .................................... B07C 5/342
[52] U.S. Cl. ........................ 209/3.1; 209/579; 209/906; 250/222 PC; 346/75; 356/72; 361/226; 364/413
[58] Field of Search .................... 209/3.1-3.3, 209/571, 579, 906, 127; 250/222 R, 222 PC; 356/39, 72, 73, 335, 338; 361/226; 364/413; 346/75

[56] References Cited

U.S. PATENT DOCUMENTS

| | | | |
|---|---|---|---|
| 3,380,584 | 4/1968 | Fulwyler | 209/3 |
| 3,600,955 | 8/1971 | Bischoff | 346/75 X |
| 3,710,933 | 1/1973 | Fulwyler et al. | 209/3 |
| 3,761,941 | 9/1973 | Robertson | 346/1 |
| 3,769,627 | 10/1973 | Stone | 346/75 |
| 3,826,364 | 7/1974 | Bonner et al. | 209/3.1 |
| 3,836,912 | 9/1974 | Ghougasian et al. | 346/75 |
| 3,851,169 | 11/1974 | Faxvog | 250/222 |
| 3,878,519 | 4/1975 | Eaton | 346/1 |
| 3,907,429 | 9/1975 | Kuhn et al. | 356/28 |
| 3,920,702 | 10/1975 | Corll | 356/72 |
| 3,941,479 | 3/1976 | Whitehead | 356/102 |
| 3,953,860 | 4/1976 | Fujimoto et al. | 346/75 |
| 3,963,606 | 6/1976 | Hogg | 209/3 |
| 3,982,251 | 9/1976 | Hochberg | 346/1 |
| 4,025,926 | 5/1977 | Fujimoto et al. | 346/1 |
| 4,045,770 | 8/1977 | Arnold et al. | 346/75 |
| 4,047,183 | 9/1977 | Taub | 346/1 |
| 4,047,183 | 9/1977 | Taub | 346/75 |
| 4,148,718 | 4/1979 | Fulwyler | 209/3.1 |
| 4,150,384 | 4/1979 | Meece | 346/75 |

OTHER PUBLICATIONS

"Laser Flow Microphotometry for Rapid Analysis and Sorting of Mammalian Cells" Mullaney, et al. Annals New York Academy of Sciences, vol. 267, pp. 176-190.
"Feedback for Synchronized Pressure Jet Using Optical Sensor" IBM Technical Disclosure Bulletin, vol. 16, No. 12, May 1974, pp. 3877-3878.
"Phase Detection on Ink Jet Droplets" IBM Technical Disclosure Bulletin, vol. 16, No. 3, Aug. 1973, p. 880.

Primary Examiner—Joseph J. Rolla
Attorney, Agent, or Firm—Audley A. Ciamporcero, Jr.

[57] ABSTRACT

A novel method and apparatus for automatically setting the time delay for relatively charging droplets in an electrostatic particle sorting system is disclosed. By utilizing a movable sheath sensing means for sensing the light scatter and extinction of this stream, the flow rate and distance to breakpoint are automatically measured and used to calculate and set the timing delay circuitry. This insures that droplet charging at the breakpoint will occur synchronously to produce selective relative charging of those droplets containing particles to be sorted.

26 Claims, 2 Drawing Figures

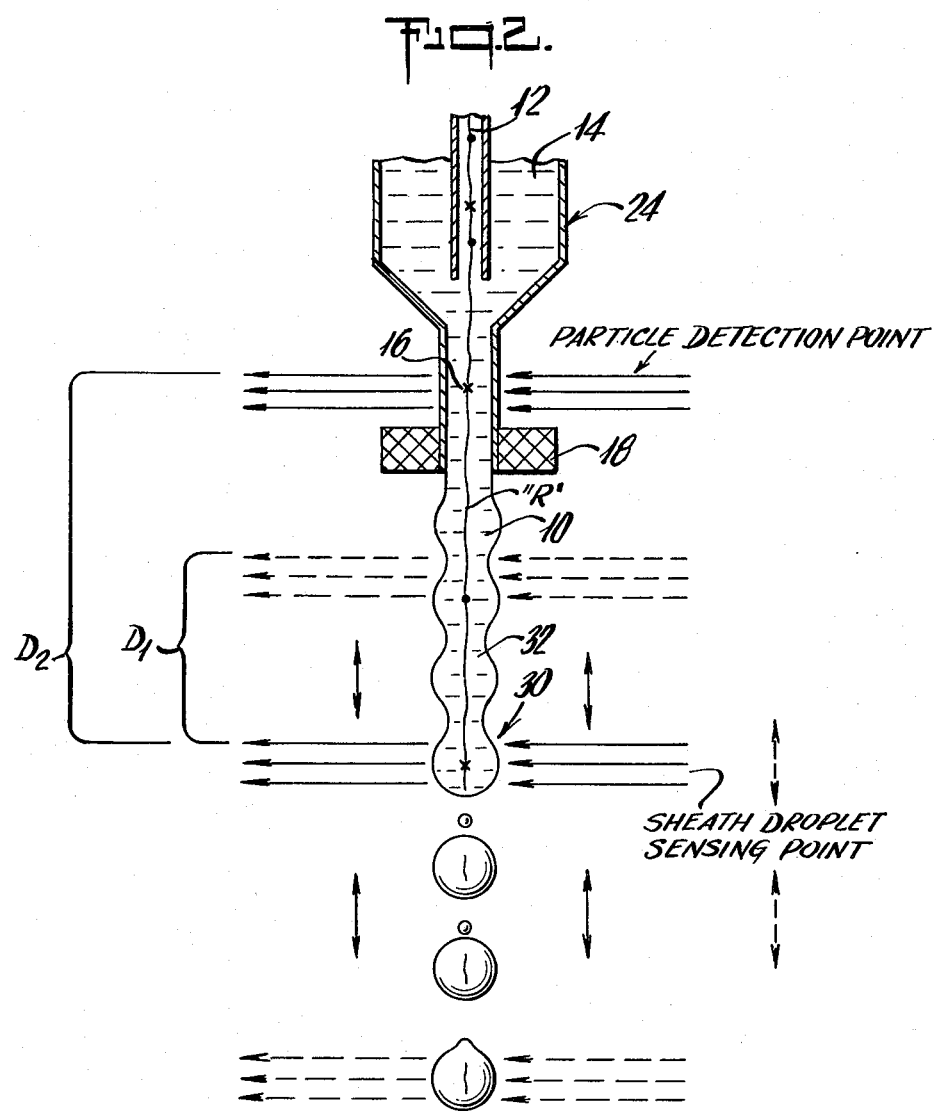

AUTOMATIC RELATIVE DROPLET CHARGING TIME DELAY SYSTEM FOR AN ELECTROSTATIC PARTICLE SORTING SYSTEM USING A RELATIVELY MOVEABLE STREAM SURFACE SENSING SYSTEM

CROSS REFERENCE TO RELATED APPLICATIONS

The present application is related to the following applications, each of which is assigned to the assignee of the present application and are hereby incorporated by reference as is fully set forth herein: The invention of Igino Lombardo, Donald E. Barry, and W. Peter Hansen entitled, "Method For Detecting And Controlling Flow Rates Of The Droplet Forming Stream Of An Electrostatis Particle Sorting Apparatus", Ser. No. 68,231, filed Aug. 20, 1979; the invention of Igino Lombardo and W. Peter Hansen entitled, "Method And Apparatus For Positioning The Point Of Droplet Formation In The Jetting Fluid Of An Electrostatic Sorting Device", Ser. No. 68,113, filed Aug. 20, 1979; the invention of Igino Lombardo and Donald E. Barry entitled, "Method For Automatically Setting The Correct Phase Of The Charge Pulses In An Electrostatic Flow Sorter", Ser. No. 68,234, filed Aug. 20, 1979; the invention of Donald E. Barry and Igino Lombardo entitled, "A Method For Measuring The Velocity Of A Perturbed Jetting Fluid In An Electrostatic Particle Sorting System", Ser. No. 68,235, filed Aug. 20, 1979; and the invention of Richard A. Dussault and Igino Lombardo entitled, "A Servo System To Control The Spatial Position Of Droplet Formation Of A Fluid Jet In A Cell Storing Apparatus", Ser. No. 68,112, filed Aug. 20, 1979.

As to Ser. No. 68,231, please see generally pages 15-25; as to Ser. No. 68,113, see generally pages 15-24; as to Ser. No. 68,234, see generally pages 15-21; as to Ser. No. 68,235, see generally pages 15-22; and as to Ser. No. 68,112, see generally pages 15-27.

BACKGROUND OF THE INVENTION

The present invention relates generally to the field of electrostatic flow sorters, and more particularly to those sorters which are adapted to sense the presence and/or character of particles in a laminar flow stream and to selectively sort those particles by breaking that stream into a number of discrete droplets, and sorting those droplets containing such preselected particles. Such sorters are known for use in sorting and analyzing cellular compositions of given biological samples, as for example in the counting/analysis of cell types for a given blood sample.

In an apparatus of this general type, laminar flow is established through an area at which a light scattering, florescence or volume measurement is taken. Once a cell of interest has been sensed, an electronic time delay is normally activated for the length of time required for the cell to cover the distance from the point of cell detection to the point of droplet formation. Droplet formation may be accomplished by vibrating a flow chamber or orifice through which the stream passes, at a frequency sufficient to cause droplet formation, usually on the order of about 40,000 cycles per second. When a cell of interest arrives at the droplet formation point, a charging pulse may be applied to charge the droplet (plus, minus, or neutral) so that as the droplet of interest enters a subsequent DC field, it may be deflected as desired for collection. A general overview of this technique is provided in "Laser Flow Microphotometry For Rapid Analysis And Sorting Of Mammalian Cells", Mullaney, et al, Annals New York Academy Of Sciences, Vol. 267, pages 176-190 (see in particular, pages 180 and FIGS. 3 and 4).

Such particle sorters are also disclosed in U.S. Pat. Nos. 3,710,933 (Fulwyler, et al) and 3,380,584 (Fulwyler) and 4,148,718 (Fulwyler). In these patents, sorting is accomplished in accordance with a selected parameter which may be size, volume, presence of radioactivity, color, florescence, light absorption or any quality capable of being translated into an electrical quantity. These patents additionally disclose single or multi parameter measurements to effect such sorting.

In order to selectively sort those droplets containing cells which are determined to be of particular interest, apparatus of this general type generally depends upon a flow rate estimate for the fluid containing a particular cell. This flow rate estimate is used to estimate the time between cell detection and the droplet breakpoint, at which selective charging of the droplet to be sorted takes place. As disclosed in U.S. Pat. No. 3,710,933, such systems are normally aligned and adjusted prior to taking cell measurements. In particular, droplet formation is normally checked by illuminating the emerging liquid jet near the flow chamber with a strobe light or equivalent light source. The strobe light is synchroflashed with respect to the oscillator frequency. Droplet formation can then be viewed using a microscope, and by varying the voltage and frequency applied to the stream perturbing transducer, droplet formation can be adjusted for a given nozzle diameter and flow rate. See U.S. Pat. No. 3,710,933, Column 11, lines 14-49.

As described particularly in U.S. Pat. No. 3,710,933, (Fulwyler, et al), by pressurizing various reservoirs with known pressures, flow rates can be estimated and cell flow rate adjusted by varying the relative pressures between the various reservoirs feeding into the flow stream. The approximate time delay between cell sensing and droplet formation (which is estimated in Fulwyler, et al to be in the order of 1400 microseconds) can be estimated so that an appropriate droplet charging generator will operate in combination with a pulse height analyzer and cell separation logic to charge the selected cell containing droplets for subsequent electrostatic sorting.

A number of factors affect the ability of a given apparatus to selectively sort one or more types of target cells from a continuous cell stream. Even assuming that the detection equipment for identifying each cell to be sorted is 100% accurate, differences in flow rate, temperature, fluid viscosity, and transducer performance can affect the time delay or location of the desired target-cell-containing droplets at the breakpoint, which is the point at which a charge pulse must be administered to insure that the target cell will be subseqently electrostatically sorted.

Heretofore, one of the methods used to adjust such a sorting apparatus involves running a test sample through that apparatus which is set or programmed to sort for one or more readily identifiable cell types. According to this procedure, the delay time is manually adjusted until those droplets which are sorted from the flow stream are found to contain the expected number of target cells. While this method, used alone or in combination with the stroboscopic method discussed above, has achieved some success in this art, it is prone to a certain degree of error, particularly during periods of extended machine use and/or changing operating conditions, such as changing sample viscosities and/or temperatures.

In U.S. Pat. No. 3,826,364 (Bonner, et al), a particle sorting method and apparatus are disclosed wherein a coaxial flow stream is released through a vibrating nozzle. Inspection (interrogation) of the stream by one or more cell sensing means for sensing cells in the stream occurs immediately downstream of the nozzle. In the Bonner, et al device, charging pulses are supplied at appropriate times for proper separation of the drops through the use of delay units which are adjusted to provide the necessary time delay to allow for travel time of the particle from the point of particle scatter detection to the point where the stream breaks into drops. Bonner states:

"With the present arrangement the delay time between observation of a particle and its capture by a separating droplet is predictable to within three drop periods. Such high degree of predictability is due primarily to the uniform velocity of the inner particle containing stream 12A of the coaxial flow jet. That is, across the inner stream 12A the stream velocity is substantially uniform whereby particles anywhere within the cross-section of the inner stream travel with the same velocity from the point of observation to the drop separation point of the stream." U.S. Pat. No. 3,826,364, Col. 7, lines 22–32.

As further explained in the Bonner, et al disclosure, the duration as well as the time of application of the charging pulse is critical to the separation of at least the droplet containing the target particle to be sorted. After describing a preferred charging pulse which will charge at least three drops, Bonner, et al states:

"Obviously, if instrument tolerances, variations, drift and like permitted, then a drop charging time sufficient to charge only two successive drops, or a single drop, could be employed." U.S. Pat. No. 3,826,364, Col. 8, lines 2–6.

As also pointed out by Bonner, et al, a drop breaking from a given flow stream carries with it a charge which is proportional to the potential between the droplet stream and the surrounding electrodes or charging surfaces at the time the drop separates from the stream. If the drop breaks off from the jet stream during the transition time from the drop charge pulse, either during the leading or trailing edge of that pulse, some intermediate value between zero and the desired full charge may be imparted to the target droplet. In the Bonner, et al apparatus, on/off transitions of the drop charging pulse are synchronized with the drop formation means, whereby charge pulse transitions may be synchronized to occur only intermediate the formation of droplets and not when droplets separate from the stream. This is made possible in the Bonner device by the provision of a variable phase control unit included in the transducer drive circuit which is adjusted for proper timing of droplet formation with the droplet charge pulse. As with the Fulwyler devices discussed above, stroboscopic illumination of the stream permits stream viewing through a suitable microscope, the stroboscopic illumination being synchronized by the drop charging pulses such that the stream, and more particularly the deflected drops, may be illuminated to ensure that the deflected drops contain the desired particles to be sorted.

More recently, various apparatus and method have been proposed for timing the application of a charge pulse so that droplets containing the particles to be sorted may be selectively charged. In U.S. Pat. No. 3,963,606 (Hogg), a particle separator is disclosed for separating particles in a fluid according to certain particle characteristics. The Hogg device includes a means for adjusting an electrical delay to be equal to the time between the emergence of a particle from a jet forming aperture to the point of break off. Hogg proposes the use of a movable scale in place of the ground glass of prior art projection microscopes, this scale being linked to a potentiometer of an RC oscillator to thereby control the oscillator's frequency. A second potentiometer for controlling the clock oscillator frequency is coupled to a height adjustment member of the aperture, this frequency being used to clock delay shift registers such that the charging pulse may easily be made to occur at the appropriate time, irrespective of fluctuations of pressure, velocity, amplitude and frequency of the droplet forming generator. See U.S. Pat. No. 3,963,606, (Hogg) Col. 2, lines 23–36. Accordingly, Hogg represents a more automated version of the stroboscopic projection microscopic techniques discussed above.

Droplet forming characteristics in a perturbed stream have also been considered in connection with the art of ink jet printing. In the ink jet printing art, where discrete ink droplets formed in an ink jet stream are electrostatically directed to form characters on a recording surface, particular attention has been paid to establishing uniform droplet formation and charging characteristics. Since the charge imparted to any given droplet at its breakpoint is proportional to its surface area, i.e., the shape of that droplet at the breakpoint, and since even slight charge variations may produce erratic deflection characteristics, ink jet printing artisans have proposed various systems for producing an ink jet stream comprising uniformly shaped and uniformly charged droplets which will exhibit predictable down stream deflection behavior. These problems are complicated by the tendency of perturbed streams to form "satellites" which not only affect the charge imparted to preceeding or succeeding droplets, but also alter the volume of those droplets, thereby correspondingly affecting print uniformity.

In the ink jet printing art, numerous systems have been proposed for sensing the characteristics of a perturbed ink jet stream, either above or below the breakpoint of that stream. U.S. Pat. No. 3,907,429 (Kuhn, et al) discloses a method and device for detecting the velocity of droplets formed from a liquid stream. According to this disclosure, discrete droplets are directed between a pair of apertures and a light source which is strobed at a selected frequency and directed towards the apertures. By detecting the time between when a first of the apertures is blocked by a droplet in the stream as indicated by the light being broken during the strobe and the time when a second of the apertures is blocked by another droplet, when the light source is counted, the velocity of the droplets may be measured and a correction of the velocity made by changing the pressure of the manifolds supplying the liquid stream. In U.S. Pat. No. 3,769,627 (Stone) an ink jet printing system using ion charging of droplets is disclosed wherein a light source and photocell located downstream from the breakpoint of a perturbed stream is used to sense the passage of discrete droplets and to time delayed charges subsequently applied thereto. Stone states:

> "Selective drop charging involves the induction of charges in the drop being formed by a surrounding charged electrode. The induced charge varies in accordance with the inducing voltage until the instant in time when the droplet physically separates from the stream. From that time on, the induced charged is trapped and remains with the drop. It is obvious, therefore, that the charging process must be carefully synchronized with the timing of the drop break off. This involves the use of complex phasing control sensors and loops. This in turn, increases the cost of the equipment.
> * * * It is an object of this invention to provide an ink drop charging system which does not depend upon the synchronization of the charging with the break off time.
> It is another object of this invention to produce an ink drop charging system, which charges drops after they break off from the ink jet stream." U.S. Pat. No. 3,769,627 (Stone), Col. 1, lines 18-35.

This method is accomplished by using the above-described photocell arrangement for the purpose of counting and synchronizing charges applied as discrete droplets pass a plurality of separate charging stations which respond to coded information applied to each station in synchronism with the passage of each drop.

As disclosed in U.S. Pat. No. 4,047,183 (Taub), efforts have also been made to control the formation and shape of droplets in an ink jet stream by sensing the surface wave profile of the continuous portion of the stream (upstream from the breakpoint) by illuminating that portion of the stream with a radiant energy source such as a laser. The surface wave profile produced by illuminating the stream is sensed to provide the fundamental and harmonic frequency components thereof, and a perturbation drive signal, the amplitude and relative phase of which is a function of the sensed frequency components, is provided for controlling the formation and shape of the droplets. After discussing the advantages and difficulties of controlling the break off geometry, particularly with the respect to the illumination of satellite formations, Taub discloses the practical desirability of measuring the ink jet stream upstream rather than downstream from the droplet break off point:

> "The ideal time to sense the frequency, phase, and amplitude components of the ink jet stream for determining drop break off characteristics is at the precise time droplets are formed therefrom. This is usually impossible to achieve, however, since the droplets are normally formed inside the charged electrode. Therefore, according to the present invention, the drop break off characteristics are determined by sensing upstream of break off, rather than downstream as taught by the prior art. The continuous portion, that is, the portion just prior to break off of the stream is sensed to determine the break off characteristics. In response to the sensed characteristics, a piezoelectric drive signal is provided which controls droplet formation, and accordingly provides increased drop charging efficiency." U.S. Pat. No. 4,047,143 (Taub), Col. 4, lines 53-68.

Taub discloses a system wherein an ink jet manifold having a perturbation means such as a piezoelectric crystal emits a perturbed ink jet stream into charge electrode structures which are pulsed in "a well known manner" to selectively apply charge to the droplets. A source of radiant energy, which may comprise a helium-neon laser, emits radiant energy focused on the continuous portion of the jet "just prior to the jet entering the charged electrode structure". "Since the ink is opaque, a shadow is formed" which is imaged through a lens onto a substrate which has a slit formed therein. The shadow formed thereby represents the surface wave profile of the jet which is a representation of the respective amplitudes and relative phases of fundamental and harmonic frequencies. Taub states:

> "The light passing through the slit 44 is influenced by the wave passing a given point on the perimeter of the jet, and accordingly is a representation of the frequency components of the jet at this particular point, as well as being indicative of the shape of a given droplet when it breaks-off downstream. It is necessary to make this slit somewhat larger than the largest diameter to be measured, typically the drop diameter, so that the clipping of the wave form does not occur, as well as preventing the generation of spurious diffraction effects. A narrow band pass filter 48, which has a band pass on the order of 100A centered in the laser wavelength, is used so measurements may be made in room light. The light passed by the filter 48 is then transmitted to a photomultiplier tube 50 which measures the intensity of the light. Therefore, the output voltage of the photomultiplier tube 50 is proportional to the diameter of the jet blocking the slit, which is to say, to the local diameter of the jet at the point being probed . . . It is to be appreciated that the signal output . . . may be applied to analyzing means 80 by other timing means such as a stepping motor, or alternatively may be applied concurrently to inputs of devices 82, 84 and 86, rather than in the time sequence described." U.S. Pat. No. 4,047,183. See Col. 6, lines 27-68, Col. 7, lines 1-26.

In Taub's preferred embodiment, the output signal so obtained is conditioned to control the fundamental and harmonic frequencies applied to the piezoelectric perturbation means for controlling the droplet formation and shape of droplets produced by the ink jet stream.

For other disclosures of ink jet printing systems using optical sensors, see IBM Technical Disclosure Bulletin Volume 16, No. 12, May 1974, Page 3877-8, entitled "Feedback For Synchronized Pressure Jet Using Optical Sensor"; and IBM Technical Disclosure Bulletin, Vol. 16, No. 3, August 1973, Page 880, entitled "Phase Detection On Ink Jet Droplets".

For other disclosures relating to various ink jet printing synchronization systems, please refer to U.S. Pat. No. 4,025,926 (Fujimoto, et al) entitled, "Phase Synchronization For Ink Jet System Printer"; U.S. Pat. No. 4,045,770 (Arnold, et al) entitled, "Method and Apparatus For Adjusting The Velocity Of Ink Drops In An Ink Jet Printer"; U.S. Pat. No. 3,953,860 (Fujimoto, et al) entitled, "Charge Amplitude Detection For Ink Jet System Printer"; U.S. Pat. No. 3,761,941 (Robertson) entitled, "Phase Control For A Drop Generating and Charging System"; U.S. Pat. No. 3,836,912 (Ghougasian, et al) entitled, "Drop Charge Sensing Apparatus For Ink Jet Printing System"; U.S. Pat. No. 3,982,251 (Hochberg) entitled, "Method and Apparatus For Recording Information On a Recording Medium"; U.S. Pat. No. 3,878,519 (Eaton) entitled, "Method and Apparatus For Synchronizing Droplet Formation In A Liquid Stream".

For other patents disclosing particle or flow sorting systems, please see U.S. Pat. No. 3,941,479 (Whitehead) entitled, "Use Of Modulated Stimulus To Improve Detection Sensitivity For Signals From Particles In A Flow Chamber"; U.S. Pat. No. 3,851,169 (Faxvog) entitled, "Apparatus For Measuring Aerosol Particles"; and U.S. Pat. No. 3,910,702 (Corll) entitled, "Apparatus For Detecting Particles Employing Apertured Light Emitting Device".

SUMMARY OF THE INVENTION

The present invention provides a novel system for automatically setting the appropriate time delay between the time of particle detection and the time when that particle has reached the breakpoint such that charging of the droplet at the breakpoint will result in the sorting of that droplet by the particle sorting system. A novel sheath sensing means is provided which is relatively movable with respect to the perturbed flow stream for the purpose of measuring both the distance between droplets and the distance between the breakpoint and the particle detection point (or a corresponding reference point which is a fixed distance from that particle detection point). From this information, the fluid velocity may be easily derived and a ratio established between that velocity and the distance between the breakpoint and particle detection point. This ratio is used to adjust time delay control electronics controlling droplet charging.

An additional feature of the system of the present invention is its ability to produce a visually observable wave form display which may provide information concerning the surface characteristics of the perturbed stream at points above, below and at the breakpoint.

Accordingly, a primary object of the present invention is the provision of an improved system for timing the application of droplet charging at the droplet breakpoint of a perturbed laminar flow stream of a particle sorting apparatus. This and other objects of the present invention will become apparent from the following more detailed description.

BRIEF DESCRIPTION OF THE DRAWINGS

FIG. 2 is an enlarged diagrammatic view of the transducer, laminar flow and droplet stream portion of the system illustrated in FIG. 1, showing relative positions between the particle detection point and various sheath/droplet sensing points, the solid lined sheath/droplet sensing point being located at the breakpoint of the perturbed flow stream, and two alternate dotted line sheath/droplet sensing points being illustrated with dotted arrows.

DESCRIPTION OF THE PREFERRED EMBODIMENTS

Figure 1:
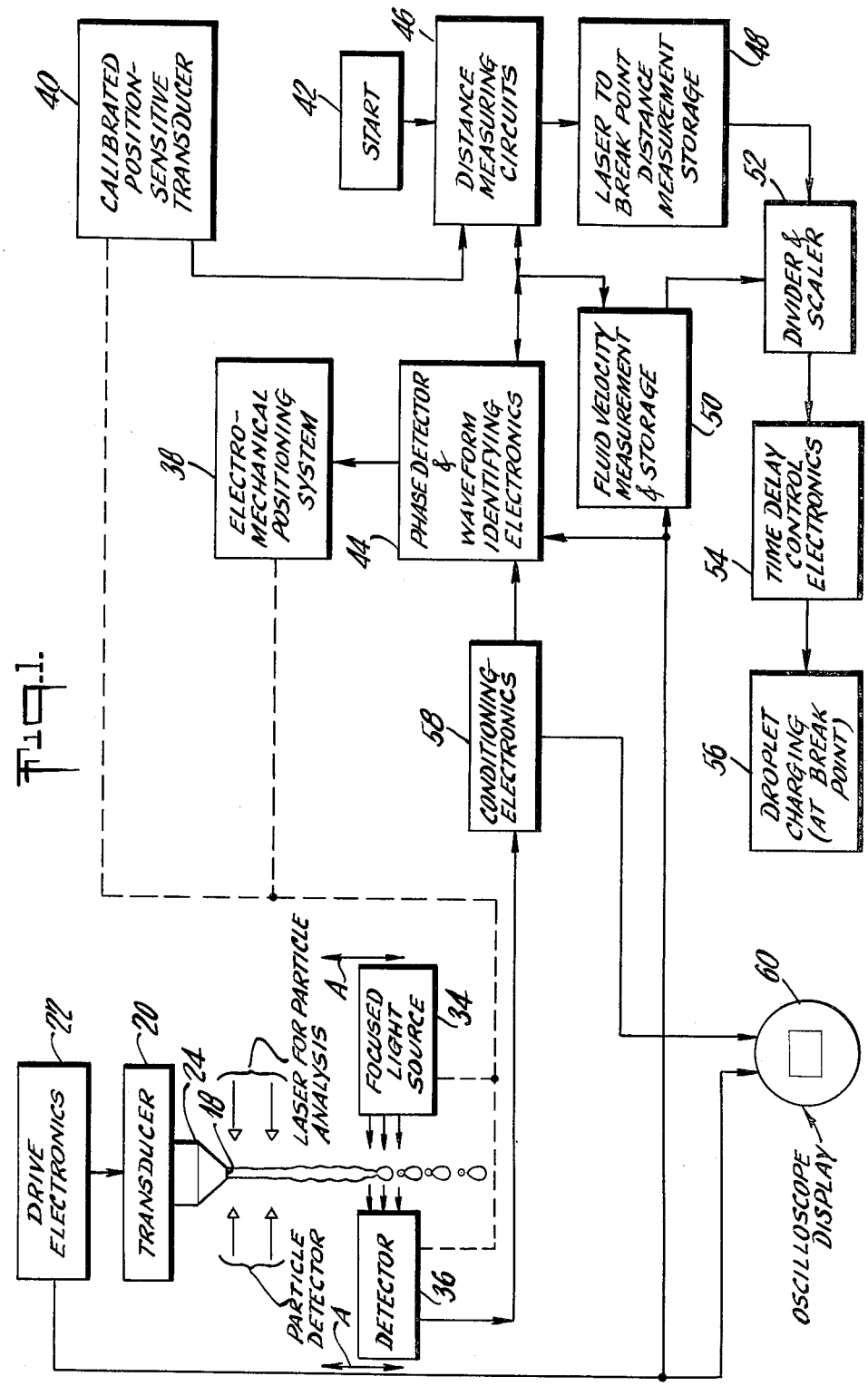
FIG. 1 is a diagrammatic block drawing of the preferred embodiment particle sorting system of the present invention.

Although specific forms of the invention have been selected for illustration in the drawings, and the following description is drawn in specific terms for the purpose of describing these forms of the invention, this description is not intended to limit the scope of the invention which is defined in the appended claims.

The present invention provides a novel method and system for automating the operation of an electrostatic flow sorter. In electrostatic flow sorters, there exists a need for determining the velocity of the jet, the distance from the point at which the particles to be sorted are analyzed to the point where droplet formation occurs, and the characteristics of the droplet stream in terms of uniformity and droplet size, satellite formation and stream stability. The system and method hereinafter described provide methods for automatically carrying out these needed determinations without the use of microscopes, as have heretofore been used in the prior art.

Referring now to FIG. 2, which is an enlarged diagrammatic view of the flow stream portion of the electrostatic particle sorting system of the present invention, a perturbed laminar flow stream 10 is established through the combination of a core stream portion 12 containing various particles to be sensed and selectively sorted, and a sheath stream portion 14 for surrounding and carrying the core stream portion at least past a particle detection point 16. The particle detection point 16 may be located above a flow chamber orifice 18 which is perturbed with a preselected frequency and amplitude by a transducer 20 which is driven by conventional transducer drive electronics 22. By contrast, the transducer 20 shown in FIG. 1 is coupled with the sheath stream/flow chamber conduit designated generally 24. One of ordinary skill in the art will recognize that various transducer flow chamber/orifice couplings may be effected provided the result thereof is the perturbation of the laminar flow stream at and/or below the orifice at a preselected frequency and amplitude. While the particle detection point illustrated in FIG. 2 of the drawings is disposed substantially above the orifice 18, as illustrated particularly in FIG. 1, the particle detection point may be located either above or immediately below that orifice, as is well known to the art. In either instance, the travel time of a detected particle, such as the particle located at particle detection point 16 to the breakpoint designated generally 30 is a critical value which must be determined in order to insure that the selected droplet charging of droplets formed at the breakpoint will contain the desired particles which have been sensed upstream.

In accordance with the preferred embodiment of the present invention, the time delay between the sensing of a particle at the particle detection point and the application of a droplet charging pulse when that particle reaches the droplet breakpoint is automatically determined through the use of a sheath sensing means for selectively sensing the light scattering and extinction character of the perturbed laminar flow stream 32 at a plurality of sheath sensing points therealong. This sheath sensing means basically comprises a radiant energy source, such as a focused light source 34 (which focuses light upon the perturbed flow stream 32) and detector 36 axially aligned on the opposite side of the flow stream for measuring the extinction or scatter of the light produced by the flow stream at that sheath sensing point. The focused light source may be a source of radiant energy with respect to which the sheath stream portion of the perturbed flow stream is essentially translucent. The sheath detector receptor 36 may be a photodiode or photomultiplier which produces a surface character output signal which is proportional to the surface character of the stream at the given sheath sensing point at which the light source is focused. In order to collect surface character information from a variety of points along the perturbed laminar flow stream 32, the focused light source is movable in response to the output of an electromechanical positioning system 38 which automatically positions the sheath sensing means at any one of a plurality of sheath sensing points along the perturbed stream. Accordingly, the sheath sensing means may be caused to move in the directions of the double ended arrows in FIG. 1 so that the sheath sensing point may be relocated to points corresponding above, at or below the breakpoint of the perturbed laminar flow stream.

Time delay between the time of sensing a particle to be sorted and the time of charging the droplet containing that particle at the breakpoint is calculated by determining the velocity of the flow stream and the distance between the particle sensing point and the laminar stream breakpoint. In order to determine the particle-sensing-point-to-breakpoint distance, a calibrated position-sensitive transducer 40 is provided coupled to the electromechanical positioning system 38 and to the movable sheath sensing means 34 and 36. A particle-sensing-point-to-breakpoint output signal may be generated thereby. This calibrated position-sensitive transducer will be calibrating the position sensitive tranducer 40 with respect to the particle detection point so that its output corresponds to a particle-sensing-point to sheath sensing point distance. Alternatively, the position-sensitive transducer 40 may be calibrated with respect to a zero reference setting "R" (FIG. 2), which is located at a preselected distance from the particle detection point. Thus, once the start circuitry 42 is activated, the electromechanical positioning system will cause the sheath sensing means to move away from this reference point until the breakpoint of the perturbed flow stream is located, as detected by waveform identifying electronics 44. The relative position of the sheath sensing point with respect to the reference point may then be transmitted by the calibrated position-sensitive transducer 40 to distance measuring circuits 46 which will calculate and store the laser-to-breakpoint distance measurement in laser to breakpoint distance measurement storage 48.

Once knowing the distance between the particle sensing point and the breakpoint, it is only necessary to calculate the velocity of the perturbed laminar flow stream in order to determine the time that will elapse between the sensing of a particle at the particle sensing point and its arrival at the breakpoint. In addition to comprising the aforementioned waveform identifying electronics, therefore, the surface character analysis means further comprises phase detector electronics which determines and controls the mechanical relocation of the sheath sensing means to produce preselected degrees of output signal phase shift. For example, the surface character analysis means will selectively move the sheath sensing points through a preselected output signal phase shift, as, for example, 360°. The distance which is traveled by the sheath sensing means, that is, the distance between the sheath sensing points before and after this phase shift is sensed by position sensitive transducer 40 and provided to the distance measuring circuits 46. If these sheath sensing points were located below the breakpoint, the distance measured by the distance measuring circuits 46 will correspond to the droplet spacing of (a non-satellite containing) flow stream. If these points were located above the breakpoint, the distance of a single perturbation cycle will have been determined. Accordingly, a velocity means 50 is provided for sensing the perturbation frequency and for providing a velocity output signal which is proportional to the product of the droplet spacing/perturbation cycle distance output signal multiplied by this perturbation frequency. The output of this fluid velocity measurement and storage means 50 is transmitted together with the output of the laser-to-breakpoint distance measurement storage 48 to a divider and scaler 52 which establishes the ratio between the velocity of the fluid and the distance which the fluid must travel from particle detection point to breakpoint. The quotient thereof is scaled for transmission to the time delay control electronics 54 which establishes the time delay for the droplet charging means 56 for relatively charging selected ones of said droplets as they are formed at said breakpoint.

In order to insure that the surface character output signal of the sheath sensing means is of a suitable quality for use by the phase detector and waveform identifying electronics, suitable conditioning electronics 58, such as filtering and amplification electronics may be interposed between the detector 36 output and these electronics. Similarly, for purposes of visual observation, an oscilloscope display 60 may be coupled to the output of the transducer drive electronics 22 and the conditioning electronics 58 for the purpose of visually observing the waveform of the surface character output signal at any desired sheath sensing point.

In FIG. 2, for example, the distances to be measured by the distance measuring circuits 46 are illustrated in combination with their various reference/detection points. As discussed above, the particle-detection-to-breakpoint distance is represented as indicated by $D_2$, whereas distance $D_1$ illustrated in FIG. 2 represents the distance sensed through a signal output phase shift of approximately 720°. As one of ordinary skill in the art will recognize, the illustrated perturbed flow stream 32 does not represent the actual shape of a perturbed flow stream, but rather is substantially simplified for the purpose of illustrating the concepts of the present invention.

The waveform identifying electronics for at least identifying the waveform at the breakpoint should distinguish the unique form of the surface character output at that breakpoint. Presently, the preferred waveform identifying electronics for use in identifying this breakpoint surface character output signal is that described in the related application of Richard A. Dussault and Igino Lombardo, entitled "A Servo System To Control The Spatial Position Of Droplet Formation Of A Fluid Jet In A Cell Sorting Apparatus", which disclosure is incorporated by reference as if fully set forth herein. Similarly, the details and optics for use in the preferred sheath sensing means are disclosed in the related applications which have been incorporated herein by reference.

As mentioned above, it is also anticipated that the sheath sensing point may be moved below the breakpoint for the purpose of observing the surface character output signal produced by droplets positioned below the breakpoint. By providing a shift means for shifting the sheath sensing points substantially below the breakpoint, it is possible to observe the droplets and/or satellites present in these locations. Accordingly, using the oscilloscope display 60, other appropriate adjustments may be made to the system to establish the desired droplet uniformity and satellite condition.

From the above, it will be seen that an extremely efficient and reliable system is described for automatically setting the time delay circuitry of a particle sorting system without resorting to the strobomicroscopic adjustment techniques heretofore known to the art.

It will be understood that various changes in the details, materials, and arrangement of parts which have been herein described and illustrated in order to explain the nature of this invention may be made by those skilled in the art within the principle and scope of the invention as expressed in the following claims. As used herein, "perturbed" or "perturbation" is meant to include not only mechanical/vibratory methods for creating discontinuities in the stream, but also discontinuities which are induced by other means such as alteration of stream surface tension, for example, by electrical, thermal, or optical means. Likewise, periodic or aperiodic perturbations are meant to be included.

It will further be understood that the "Abstract of the Disclosure" set forth above is intended to provide a non-legal technical statement of the contents of the disclosure in compliance with the Rules of Federal Practice of the U.S. Patent and Trademark Office, and is not intended to limit the scope of the invention described and claimed herein.

What is claimed is:

1. An electrostatic particle sorting system, comprising:
   (a) flow means for establishing the flow of a continuous particle containing stream comprising at least a particle containing core stream portion and a surrounding sheath stream portion, said stream having a particle sensing point defined therealong;
   (b) optical detection means for optically detecting said particles at least at said particle sensing point;
   (c) perturbation means for perturbing said stream with at least a preselected frequency and amplitude to cause said stream to form a breakpoint at which said stream becomes a series of discrete droplets;
   (d) droplet charging means for relatively charging selected ones of said droplets as they are formed at said breakpoint; and
   (e) synchronization means for timing said relative charging such that said selected droplets contain at least selected particles detected by said optical detection means, said synchronization means comprising: sheath sensing means for selectively sensing at least the light scatter characteristic of said stream at any of a plurality of sheath sensing points therealong and for selectively producing any of a plurality of surface character output signals, each of which is proportional to the surface character of said stream at one of said plurality of sheath sensing points.

2. The invention of claim 1 wherein said synchronization means further comprises means for measuring the distance between at least two of said plurality of sheath sensing points.

3. The invention of claim 1 wherein said synchronization means further comprises shift means for selectively moving said sheath sensing means between said sheath sensing points.

4. The invention of claim 1 wherein said synchronization means further comprises surface character analysis means for producing at least one output signal responsive to said sheath sensing means, said analysis means comprising velocity means for producing a velocity output signal which is at least proportional to the velocity of said stream.

5. The invention of claim 4 wherein said surface character analysis means further comprises distance means for producing a particle-sensing-point-to-break-point output signal which is at least proportional to the distance between said breakpoint and said particle sensing point.

6. The invention of claim 5 wherein said surface character analysis means further comprises a scaler-divider means for producing a ratio output signal which is proportional to the ratio between said particle-sensing-point-to-breakpoint signal and said velocity output signal.

7. The invention of claim 6 wherein said synchronization means further comprises time delay control means responsive to said ratio output signal for adjusting the timing of said droplet charging means.

8. The invention of claim 5 wherein said synchronization means comprises surface character analysis means for at least detecting the phase of said surface character output signal.

9. The invention of claim 8 wherein said surface character analysis means further comprises means for identifying at least the breakpoint waveform of said surface character output signal.

10. The invention of claim 9 wherein said synchronization means further comprises shift means for selectively moving said sheath sensing points, said shift means being selectively responsive to said surface character analysis means for selectively moving said sheath sensing points until said output signal undergoes a preselected phase shift.

11. The invention of claim 10 wherein said velocity means further comprises droplet spacing means for measuring the distance between said sheath sensing points spaced apart according to said preselected phase shift and for producing a droplet spacing output signal which is proportional thereto.

12. The invention of claim 11 wherein in said velocity means further senses said perturbation frequency, said velocity output signal being proportional to the product of said droplet spacing output signal times said perturbation frequency.

13. A method of electrostatically sorting particles, comprising the steps of:
   (a) establishing the flow of a continuous particle containing stream comprising at least a particle containing core stream portion and a surrounding sheath stream portion, said stream having a particle sensing point defined therealong;
   (b) optically detecting said particles at least at said particle sensing point;
   (c) perturbing said stream with at least a preselected frequency and amplitude at a preselected perturbation point defined therealong to cause said stream to form a breakpoint at which said stream becomes a series of discrete droplets;
   (d) relatively charging selected ones of said droplets as they are formed at said breakpoint; and
   (e) synchronizing said relative charging such that said selected droplets contain at least selected particles detected by said optical detection step, said synchronizing steps of selectively sensing at least the light scatter characteristic of at least the sheath portion of said stream at a plurality of sheath sensing points defined therealong to produce a plurality of surface character output signals, each of which is proportional to the surface character of the stream at one of said plurality of said sheath sensing points.

14. The method of claim 13 wherein said synchronizing step further comprises the step of measuring the distance between at least two of said plurality of sheath sensing points.

15. The method of claim 13 wherein said synchronizing step further comprises the step of sequentially sensing said stream at said sheath sensing points.

16. The invention of claim 13 wherein said synchronizing step further comprises the step of analyzing said surface character output signals to generate a velocity output signal which is at least proportional to the velocity of said stream.

17. The invention of claim 16 wherein said synchronizing step further comprises the step of measuring the distance between said particle sensing point and said breakpoint to generate a particle-sensing-point-to-breakpoint output signal which is at least proportional to said measured distance.

18. The invention of claim 17 wherein said synchronizing step further comprises the step of scaling and dividing said particle sensing point to breakpoint signal and said velocity output signal to produce a ratio output signal proportional to the ratio therebetween.

19. The invention of claim 18 wherein said synchronizing step further comprises the step of adjusting the timing of said droplet charging in response to said ratio output signal.

20. The invention of claim 17 wherein said synchronizing step comprises the step of analyzing said surface character output signal for at least detecting the phase thereof.

21. The invention of claim 20 wherein said analyzing step further comprises the step of identifying at least a breakpoint waveform of said surface character output signal.

22. The invention of claim 21 further comprises the step of selectively moving the sheath sensing point in response to said analysis of the surface character of said sheath stream portion until said surface character output signal undergoes a preselected phase shift.

23. The invention of claim 22 wherein said step of determining the velocity of said stream further comprises the step of measuring the distance between a plurality of sheath sensing points spaced apart according to said preselected phase shift, and producing a droplet spacing output signal which is proportional thereto.

24. The invention of claim 23 wherein said step of detecting said velocity further comprises the step of sensing said perturbation frequency to produce a velocity output signal which is proportional to the product of said droplet spacing output signal times said perturbation frequency.

25. An electrostatic particle sorting system, comprising:
  (a) flow means for establishing the flow of a continuous particle containing stream comprising at least a particle containing core stream portion and a surrounding sheath stream portion, said stream having a particle sensing point defined therealong;
  (b) detection means for detecting said particles at least at said particle sensing point;
  (c) perturbation means for perturbing said stream with at least a preselected frequency and amplitude to cause said stream to form a breakpoint at which said stream becomes a series of discrete droplets;
  (d) droplet charging means for relatively charging selected ones of said droplets as they are formed at said breakpoint; and
  (e) synchronization means for timing said relative charging such that said selected droplets contain at least selected particles detected by said detection means, said synchronization means comprising: sheath sensing means for selectively sensing at least the light scatter characteristic of said stream at any of a plurality of sheath sensing points therealong and for selectively producing any of a plurality of surface character output signals, each of which is proportional to the surface character of said stream at one of said plurality of sheath sensing points.

26. A method of electrostatically sorting particles, comprising the steps of:
  (a) establishing the flow of a continuous particle containing stream comprising at least a particle containing core stream portion and a surrounding sheath stream portion, said stream having a particle sensing point defined therealong;
  (b) detecting said particles at least at said particle sensing point;
  (c) perturbing said stream with at least a preselected frequency and amplitude at a preselected perturbation point defined therealong to cause said stream to form a breakpoint at which said stream becomes a series of discrete droplets;
  (d) relatively charging selected ones of said droplets as they are formed at said breakpoint; and
  (e) synchronizing said relative charging such that said selected droplets contain at least selected particles detected by said detection step, said synchronizing steps of selectively sensing at least the light scatter characteristic of at least the sheath portion of said stream at a plurality of sheath sensing points defined therealong to produce a plurality of surface character output signals, each of which is proportional to the surface character of the stream at one of said plurality of said sheath sensing points.

* * * * *